United States Patent [19]

Lantero, Jr.

[11] 4,390,627
[45] Jun. 28, 1983

[54] IMMOBILIZATION OF THE SUCROSE MUTASE IN WHOLE CELLS OF PROTAMINOBACTER RUBRUM

[75] Inventor: Oreste J. Lantero, Jr., Goshen, Ind.

[73] Assignee: Miles Laboratories, Inc., Elkhart, Ind.

[21] Appl. No.: 315,191

[22] Filed: Oct. 26, 1981

[51] Int. Cl.$^3$ .................. C12N 11/08; C12P 19/12; C12N 11/02; C12N 11/06

[52] U.S. Cl. ............................ 435/180; 435/100; 435/177; 435/181; 435/233

[58] Field of Search ............... 435/174, 177, 178, 180, 435/181, 100, 233

[56] References Cited

U.S. PATENT DOCUMENTS

| | | | |
|---|---|---|---|
| 3,736,231 | 5/1973 | Stanley et al. | 435/177 |
| 3,779,869 | 12/1973 | Zienty | 195/68 |
| 3,980,521 | 9/1976 | Amotz et al. | 435/174 |
| 3,989,596 | 11/1976 | Long | 195/56 |
| 4,060,456 | 11/1979 | Long | 195/31 |
| 4,090,919 | 5/1978 | Chibata et al. | 435/177 X |
| 4,212,943 | 7/1980 | Borglum | 435/180 |
| 4,224,411 | 9/1980 | Chibata et al. | 435/177 |
| 4,288,552 | 9/1981 | Gestrelius | 435/174 |
| 4,337,313 | 6/1982 | Hershberger et al. | 435/180 X |
| 4,355,105 | 10/1982 | Lantero, Jr. | 435/233 X |

OTHER PUBLICATIONS

Ono, et al.–Agric. Biol. Chem., 42 1847–1853 (1978).
Ohba, et al.–Biotechnology and Broengineering, vol. XX, pp. 665–676 (1978).

*Primary Examiner*—David M. Naff
*Attorney, Agent, or Firm*—Jerome L. Jeffers

[57] ABSTRACT

Sucrose mutase in whole cells of *Protaminobacter rubrum* is immobilized by contacting the cells with tannic acid, polyethylenimine, and an adduct of glutaraldehyde and an epihalohydrin/polyamine copolymer. The resultant reaction product has improved sucrose mutase activity and physical characteristics for use in a packed-bed reactor to convert sucrose to palatinose.

5 Claims, No Drawings

IMMOBILIZATION OF THE SUCROSE MUTASE IN WHOLE CELLS OF PROTAMINOBACTER RUBRUM

BACKGROUND OF THE INVENTION

The use of enzymes derived from microbial cells to effect specific chemical transformations is well known. The free cells can be used efficiently in a batch-type process but do not lend themselves to continuous, industrial scale processes. This difficulty has led to an increased interest in the preparation of various forms of immobilized enzymes.

U.S. Pat. No. 3,779,869 (issued Dec. 18, 1973) discloses the stabilization of glucose isomerase activity by treating whole bacterial cells with glutaraldehyde. U.S. Pat. No. 4,060,456 (issued Nov. 29, 1977) involves the stabilization of microbial cell material having glucose isomerase activity by treating it with a cationic, polyelectrolyte flocculating agent such as a polyethylenimine or polyvinylpyrrolidone. The use of polyelectrolytes such as polyamines and cationic, polyacrylamides in the stabilization of microbial cells having active enzymes associated therewith is disclosed in U.S. Pat. No. 3,989,596 (issued Nov. 2, 1976).

Ono et al describe the immobilization of naringinase from *Aspergillus niger* by adsorbing the enzyme to tannin-aminohexyl cellulose prepared by the reaction of aminohexyl cellulose and cyanogen bromide activated Chinese gallotannin in *Agric. Biol. Chem.*, 42(10), 1847–1853 (1978). Ohba et al disclose in *Biotechnology and Bioengineering*, Vol. XX, Pp. 665–676 (1978) that pullulanase can be successfully immobilized by the addition of tannic acid to the culture filtrate of thermophilic *Streptomyces flavochromogenes* to form a tannin-pullulanase adduct which can then be bound to TEAE-cellulose.

There is disclosed in U.S. Pat. No. 4,212,943 (issued July 15, 1980) a bacterial cell aggregate having increased particle hardness which is produced by contacting a mass of bacterial cells with a cross-linked reaction product of glutaraldehyde or cyanuric halide and a cationic polymer obtained by polymerization of an epihalohydrin and an alkylenepolyamine. Copending application Ser. No. 214,218 filed Dec. 8, 1980, now U.S. Pat. No. 4,337,313 discloses the immobilization of biocatalysts, including whole cells of the species *Protaminobacter rubrum*, by treatment with tannin and an adduct of glutaraldehyde and an epihalohydrin/polyamine copolymer.

The biocatalytic conversion of sucrose to palatinose is known. Hydrogenation of palatinose provides Palatinit, a noncaloric sweetener. The biocatalytic conversion can be accomplished by contacting viable cells of *Protaminobacter rubrum* containing sucrose-mutase activity with a sucrose containing medium. This conversion is carried out in a batchtype process, the economics of which would be improved by the immobilization of the biocatalyst to form particles possessing physical characteristics which would render it suitable for use in a packed-bed reactor in which the particles retain their biocatalytic activity during a continuous flow conversion of sucrose to palatinose.

SUMMARY OF THE INVENTION

The present invention is a method for the immobilization of the sucrose mutase in whole cells of the species *Protaminobacter rubrum* which comprises the steps of
(a) providing an aqueous medium containing the microorganism cells;
(b) adding tannic acid to the aqueous medium;
(c) adding polyethylenimine to the aqueous medium;
(d) adding an adduct of an epihalohydrin/polyamine copolymer and glutaraldehyde to the aqueous medium to form a reaction product;
(e) removing the reaction product from the aqueous medium; and
(f) drying the reaction product.

DETAILED DESCRIPTION

The aqueous medium containing whole cells of *P. rubrum* can be prepared by inocculating a medium consisting of the appropriate nutrients with a biologically pure culture of the microorganism. The first step in the cell immobilization process involves introducing tannic acid, preferably that obtained from quebracho, to the aqueous medium containing the microorganism cells. Typically, an amount of tannic acid equal to from 5 to 25 weight percent of the microorganism cells is employed with an amount equal to about 14 weight percent being preferred.

Normally some cell flocculation is achieved by the addition of tannic acid and additional flocculation is achieved by the addition of polyethylenimine to the aqueous medium. Polyethylenimine with a molecular weight range of from about 300 to 100,000 is suitable with a molecular weight of about 60,000 being preferred. The amount of polyethylenimine is typically in the range of from about 2 to 25 weight percent of the cells to be immobilized and preferably about 15 weight percent of such cells.

The epihalohydrin/polyamine-glutaraldehyde adduct is prepared by mixing the polymer with an aqueous solution of glutaraldehyde. In a typical laboratory scale procedure, the adduct is prepared as follows:

A preparation of the epihalohydrin/polyamine copolymer is mixed with glutaraldehyde by adding the copolymer to an aqueous glutaraldehyde solution of about 3.5% (w/w) concentration. The copolymer is in the form of its prediluted water solution which contains about 2% solids and whose pH has been adjusted to 9.0. This procedure provides a final mixture containing 1.77 g./dl. glutaraldehyde and 1.3 g./dl. copolymer. The adduct, prepared in this manner, can then be added directly to the partially flocculated microorganism solution. Typically, the weight ratio of copolymer to glutaraldehyde in the adduct is from 1:3.3 to 8.6:1 and the weight percent adduct of the microorganism cells is from 25 to 95. A preferred copolymer, because of its proven compatibility with food processing, is an epihalohydrin polyamine copolymer commercially available under the trademark BETZ 1180 from Betz Laboratories, Inc., Trevose, Pa. BETZ 1180 has a molecular weight less than one million, contains about 0.288 millimoles of amino groups per gram of solution (based on ninhydrin assay) and is marketed as a solution containing 30 weight percent solids, based on total solution weight. This compound is disclosed in U.S. Pat. Nos. 3,915,904 and 3,953,330. The compound is described therein as a water soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C.

The immobilized *P. rubrum* cells are recovered from the solution by filtration or centrifugation and dried whereupon they can be used to convert sucrose to palatinose in conventional fixed bed column reactors.

The method of practicing the present invention is further illustrated by the following examples in which the fermentation broths were prepared by inoculating a medium consisting of sugarbeet thick juice, dibasic ammonium phosphate and filtered corn steep liquor with a phage resistant mutant from a strain of *P. rubrum* deposited at the official European Centraalbureau Voor Schimmel in Born Netherlands under deposit number CBS 574.77.

The tannic acid used was quebracho tannin obtained from E. Monnier, Inc. and the PEI was PEI-600 (molecular weight of 60,000) obtained from Dow Chemical Co. The Betz:glutaraldehyde adduct was prepared by the same technique in each experiment.

EXAMPLE I

A. TANNIN-PEI-BETZ 1180:GA

To 1 liter of fermentation broth (pH 5.06) was added 25 ml. of 4% (w/v) tannic acid. The addition of the tannic acid caused a slight flocculation. After standing for 30 minutes, 30 ml. of a 4% (w/v) polyethyleneimine solution adjusted to pH 9.0 was added. Addition of the PEI increased the pH of the cell mixture from 5.01 to 5.93 with only a modest increase in flocculation. The pH of the cell mixture was then adjusted to 6.5 with dilute (1N) NaOH. Then 40 ml. of a Betz:glutaraldehyde adduct was slowly added while gently stirring. This adduct was prepared as follows:
1. 11.67 gm. of Betz 1180 was diluted to 100 ml. with wqater.
2. 17.8 ml. of 25% glutaraldheyde was diluted to 100 ml. with water.
3. The Betz 1180 solution was added to the glutaraldehyde slowly while mixing and the pH of the mixture was adjusted to 9.0.

The addition of the Betz:glutaraldehyde caused very heavy flocculation to occur which rapidly settled leaving a water clear supernatant. The cell flocculant was collected by filtration on a Buchner funnel and washed with water to provide 23.95 gm. of wet cake (70.5% moisture). A portion of the cake was extruded through an approximately 1.0 mm orifice by means of a 25 ml. plastic syringe. Both the extrudate and the remainder of the cake were dried in a 55° C. forced air oven.

The following examples were conducted leaving out one of the components of the immobilization formulation described above.

B. TANNIN-BETZ 1180:GA

One liter of fermentation broth was treated as in A above except that no polyethylenimine and a total of 120 ml. of Betz 1180:glutaraldehyde adduct was added. The cells were observed to flocculate very well leaving a water clear supernatant in the interflocculant fluid. A total of 27.01 gm. of wet cake (73.0% moisture) was obtained.

C. TANNIN-BETZ 1180:GA

One liter of fermentation broth was treated similarly to that described in B above except that only 76 ml. of the Betz 1180:glutaraldehyde adduct was added. Even though the amount of adduct was reduced to 63% of that in B, the flocculant appeared similar to that described above. A total of 26.68 gm. of wet cake (74.2% moisture) was obtained.

D. PEI-BETZ 1180:GA

To one liter of fermentation broth (pH 5.01) was added 30 ml. of 4% polyethylenimine which increased the pH to 5.96 and did not cause any apparent flocculation. The pH was adjusted to 6.5 whereupon 50 ml. of Betz 1180:glutaraldehyde adduct was added. A well formed flocculant formed which settled rapidly leaving a water clear supernatant. A 20.93 gm. wet cake (78.9% moisture) was obtained.

The following table summarizes the yield of dry material obtained and the relative immobilized activity per liter of fermentation broth. The yield (gm DS/l) is the amount of dry solids obtained per liter of fermentation broth. The sucrose-mutase activity of the immobilized preparations was estimated by stirring finely ground particles in a pH 7.0 buffered sucrose solution at 30° C. The enzyme activity was related to the amount of reducing sugars formed during the incubation by an appropriate chemical method using dinitrosalicylic acid. The five component system (Ex.A) gave the highest immobilized enzyme activity. The PEI-Betz:GA (Ex.D) resulted in a substantial decrease in immobilized enzyme activity although the activity was much greater than that from Ex.B and C. Furthermore, the hydrated particles from Ex.D of the size suitable for columnar packed bed reactors were noticeably softer than any of the other preparations.

| Preparation | Yield (gm DS/l) | Relative Immobilized Enzyme Activity Per Liter Fermentation Broth |
| --- | --- | --- |
| Example A Tannin-PEI-Betz:GA | 7.07 | 100 |
| Example B Tannin-Betz:GA | 7.29 | 18.3 |
| Example C Tannin-Betz:GA | 6.88 | 31.3 |
| Example D PEI-Betz:GA | 4.84 | 87.3 |

What is claimed is:
1. A method for the immobilization of the sucrose mutase in a microorganism of the species *Protaminobacter rubrum* which comprises the steps of:
   (a) providing an aqueous medium containing the microorganism cells;

(b) adding tannic acid to the aqueous medium in an amount of from 5 to 25 weight percent of the microorganism cells;
(c) adding polyethylenimine of a molecular weight of from about 300 to 100,000 to the aqueous medium in an amount of from about 2 to 25 weight percent of the microorganism cells;
(d) adding an adduct of an epihalohydrin/polyamine copolymer which is a water soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C. and glutaraldehyde wherein the weight ratio of copolymer to glutaraldehyde in the adduct is from 1:3.3 to 8.6:1 and the adduct's weight percent of the microorganism cells is from 25 to 95 to form a reaction product;
(e) removing the reaction product from the aqueous medium; and
(f) drying the reaction product.

2. The method of claim 1 wherein the tannic acid is quebracho tannin.

3. The method of claim 1 wherein the tannic acid is added in an amount equal to about 14 weight percent of the microorganism cells.

4. The method of claim 1 wherein the polyethylenimine has a molecular weight of about 60,000.

5. The method of claim 1 wherein polyethylenimine is added in an amount equal to about 15 weight percent of the microorganism cells.

* * * * *